(12) United States Patent
Kosaka et al.

(10) Patent No.: US 8,460,877 B2
(45) Date of Patent: Jun. 11, 2013

(54) METHOD OF PROTEIN MEASUREMENT

(75) Inventors: Hideko Kosaka, Kyoto (JP); Hisashi Sakamoto, Kyoto (JP)

(73) Assignee: Arkray, Inc., Kyoto-Shi (JP)

( * ) Notice: Subject to any disclaimer, the term of this patent is extended or adjusted under 35 U.S.C. 154(b) by 1607 days.

(21) Appl. No.: 10/586,774

(22) PCT Filed: Jan. 21, 2005

(86) PCT No.: PCT/JP2005/000758
§ 371 (c)(1),
(2), (4) Date: Jul. 21, 2006

(87) PCT Pub. No.: WO2005/071420
PCT Pub. Date: Aug. 4, 2005

(65) Prior Publication Data
US 2008/0241850 A1    Oct. 2, 2008

(30) Foreign Application Priority Data
Jan. 23, 2004   (JP) .................................. 2004-016146

(51) Int. Cl.
*G01N 33/53* (2006.01)
*G01N 33/532* (2006.01)
*G01N 33/533* (2006.01)
*G01N 21/76* (2006.01)

(52) U.S. Cl.
USPC ............. 435/7.1; 436/544; 436/546; 436/172

(58) Field of Classification Search
None
See application file for complete search history.

(56) References Cited

U.S. PATENT DOCUMENTS

| | | |
|---|---|---|
| 4,260,777 A | 4/1981 | Rittersdorf et al. |
| 5,049,358 A | 9/1991 | Lau |
| 5,385,847 A | 1/1995 | Yip et al. |
| 5,591,645 A | 1/1997 | Rosenstein |
| 5,796,476 A | 8/1998 | Wang et al. |
| 6,306,660 B1 | 10/2001 | Messenger et al. |

FOREIGN PATENT DOCUMENTS

| | | |
|---|---|---|
| EP | 0 254 081 | 1/1988 |
| EP | 909953 A2 * | 4/1999 |
| EP | 1 033 575 | 9/2000 |
| JP | 52-78866 | 7/1977 |
| JP | 61-155757 | 7/1986 |
| JP | 63-127160 | 5/1988 |
| JP | 64-63865 | 3/1989 |
| JP | 2-122264 | 5/1990 |
| JP | 5-209836 | 8/1993 |
| JP | 7-198719 | 8/1995 |
| JP | 9-79982 | 3/1997 |
| JP | 10-73592 | 3/1998 |
| JP | 11-190735 | 7/1999 |
| JP | 2002-116203 | 4/2002 |
| WO | WO 96/34271 | 10/1996 |
| WO | WO 03/001213 | 1/2003 |

OTHER PUBLICATIONS

Waheed et al. "Mechanism of dye binding in the protein assay using eosin dyes", *Analytical Biochemistry*, vol. 287, pp. 73-79 (2000).
Hong et al. "An eosin Y method for protein determination in solution", *Analytical Letters*, vol. 32, No. 12, pp. 2427-2442 (1999).
Forker et al. "Hepatic transport and binding of rose bengal in the presence of albumin and gamma globulin", *American Journal Physiology*, vol. 248, No. 6, Pt. 1, pp. G702-G708 (1985).

* cited by examiner

*Primary Examiner* — Shafiqul Haq
(74) *Attorney, Agent, or Firm* — Fox Rothschild LLP

(57) ABSTRACT

The present invention relates to a technique of measuring a protein based on a degree of coloring in a liquid sample mixed with a protein measurement indicator. In the present invention, information reflecting creatinine concentration in the liquid sample is obtained, and then an influence quantity caused by creatinine to the protein concentration measurement is eliminated based on the information.

14 Claims, 3 Drawing Sheets

METHOD OF PROTEIN MEASUREMENT

FIELD OF THE INVENTION

The present invention relates to a technique for measuring a protein contained in a liquid sample.

BACKGROUND ART

Blood contains many kinds of proteins essential for supporting life. Of these proteins, albumin occupies the largest part in quantity and has many important functions.

Albumin in the blood makes fat soluble, while making a bond with substances harmful to living organism, thereby carrying these substances to the liver. Further, albumin plays an important role in maintaining the blood osmotic pressure. Albumin is also present in urine by a very small amount. The amount of albumin in urine reflects, for example, the level of filtering function of the glomeruli in the kidneys. An increase in the amount of urinary albumin indicates that the filtering function of the glomeruli in the kidneys may have deteriorated. If the increase of urinary albumin is not taken care of, one may suffer albuminuria, which is often symptomatic of kidney disease such as chronic nephritis. If such a disease is found, dialysis must be performed, and much worse, the patient may have kidney implanting surgery. In light of these, it is important to monitor the amount of albumin in urine so that an malfunction of the kidney can be found at an early stage.

As a technique which is usable for measurement of protein such as albumin, there is a simple measurement method called immunochromatography (see Patent Documents 1 and 2). The method is carried out by using an analytical element or a capillary strip containing a labeled antibody provided in a first region and a capture antibody (anti-albumin antibody) provided in a second region. More specifically, a liquid sample (urine for example) is supplied to the first region, whereupon capillary action of the strip causes the labeled antibody and the liquid sample to move to the second region. If the liquid sample contains the detection target antigen (albumin), the antigen combines with the labeled antibody as being moved to the second region. At the second region, the antigen-antibody combination is captured by the capture antibody. Then, based on the coloring of the antigen-antibody combination in the second region, it is possible to make a visual, qualitative determination on whether or not the urine contains a greater amount of protein than a predetermined level.

The immunochromatography is a qualitative method that enables visual determination of whether the result is negative or positive, so it is useful as a preliminary check for a functional impairment in the kidney. However, the immunochromatography is disadvantageous in that it cannot specify the level of the renal impairment quantitatively. In addition, the measurement takes a long time, often 10-15 minutes, until the liquid sample has completed its movement along the strip.

On the other hand, simple quantitative methods have been proposed for measuring the protein concentration. Well known examples are protein error method and dye binding method (see Patent Documents 3 and 4). The protein error method makes use of a phenomenon that a pH indicator called protein error indicator gives a color at a higher pH than the true pH, in proportion to the amount of protein contained in the sample. The dye binding method, on the other hand, makes use of a phenomenon that a maximum absorption wavelength of a dye shifts when the dye is combined with protein.

The protein error method and the dye binding method are highly convenient because they are simple methods to use. On the contrary, accurate measurement of protein is difficult in the protein error method and the dye binding method because the reagents used commonly in these measurement methods do not have high specificity to urinary albumin and therefore affected by a number of substances which are present in the urine. To date, various improvement efforts have been made for the protein error method and the dye binding method in order to increase measurement accuracy for example. Yet, there is still room for improvement in the protein error method and the dye binding method in the field of measurement accuracy for example.

There are methods which are less susceptible to influences from coexisting substances in urine. Examples include use of metal colloid (see Patent Document 5 for example), immunoturbidimetric method, and immunolatex agglutination method. In the colloidal metal method, a membrane is used to absorb protein. The membrane is then washed to remove coexisting substances. Then metal colloid is combined with the protein to determine quantity of the protein from the color of the metal colloid. The method is certainly less susceptible to influences from the coexisting substances, but is disadvantageous in that it requires complicated measurement operations such as the step of adsorbing protein in a membrane, the step of washing, and the step of allowing the metal colloid to combine with the protein. On the other hand, the immunoturbidimetric method and the immunolatex agglutination method are disadvantageous in terms of measurement cost since they require expensive regions.

Patent Document 1: JP-B-H07-13640
Patent Document 2: JP-A-H10-73592
Patent Document 3: JP-B-S57-51627
Patent Document 4: JP-A-S61-155757
Patent Document 5: JP-A-S63-127160

DISCLOSURE OF THE INVENTION

An object of the present invention is to provide an easy, cost-advantageous and accurate method for quantifying a protein (e.g. albumin) in a liquid sample.

In order to achieve the above-described object, diligent examinations were made by the inventors. As a result, the inventors found that in albumin quantification using a specific protein measurement indicator, creatinine and albumin show similar behavioral patterns to this protein measurement indicator. In other words, the present invention is based on this finding that creatinine reacts with a specific protein measurement indicator, thereby functioning as an error factor, influencing the quantification of albumin.

Specifically, the present invention provides a method for measuring a concentration of a protein (e.g. albumin) in a liquid sample (e.g. urine, blood and cerebrospinal fluid). In this method, information which reflects an influence of the creatinine concentration in the liquid sample is obtained, and then, based on this information, the influence of creatinine on the protein concentration measurement is eliminated.

The method of measuring a protein according to the present invention includes: a first step of obtaining a first response value which is correlated with a protein concentration in the liquid sample, based e.g. on coloring given by a system containing the liquid sample and a protein measurement indicator; a second step of obtaining a second response value which is correlated with a creatinine concentration in the liquid sample in a system containing the liquid sample but not containing the protein measurement indicator; and a third step of calculating a concentration of the protein in the liquid sample, taking the second response value into consideration and based on the first response value.

Here is a specific method of eliminating the influence caused by the amount of creatinine. For example, in the second step, an influence caused by the amount of creatinine to the first response value is calculated based on the second response value, and then in the third step, a protein concentration is calculated as a preliminary value based on the first response value, and then a final protein concentration is calculated by subtracting the influence quantity of the amount of creatinine from the preliminary value. Another method of eliminating the influence caused by the amount of creatinine is as follows: In the third step, a corrected response value is obtained by correcting the first response value based on the first and the second response values, and then a protein concentration in the liquid sample is calculated based on the corrected response value.

It is noted here that the method of measuring a protein according to the present invention provides an example, in which a creatinine concentration is measured, and then a final protein concentration is calculated based on this creatinine concentration. This process is different from conventional creatinine correction.

Specifically, the conventional creatinine correction equalizes a difference in measuring condition caused by dilution or concentration of urine for example, when the liquid sample is urine. More specifically, the albumin concentration is divided by the creatinine concentration to obtain protein concentrations under a hypothetical, universal measuring condition. On the contrary, according to the method of measuring a protein offered by the present invention, an increase in the first response value caused by creatinine's reaction with the protein measuring reagent is grasped by measuring the creatinine concentration, separately from the dilution/concentration problem. Then the amount of increase is virtually offset from the response value, and the protein measurement is based on this response value. In other words, a creatinine concentration obtained for the conventional purpose of creatinine correction can be used as a creatinine concentration for the method of measuring a protein according to the present invention.

According to the present invention, a creatinine concentration (or a response which is correlated with the creatinine concentration) in a liquid sample is grasped, and then the influence on the protein concentration by the creatinine concentration is eliminated. Therefore, according to the present invention, it is possible to obtain accurate measurements without creatinine influence, by an easy and cost-advantageous method using a protein measurement indicator.

BEST MODE FOR CARRYING OUT THE INVENTION

Figure 1:
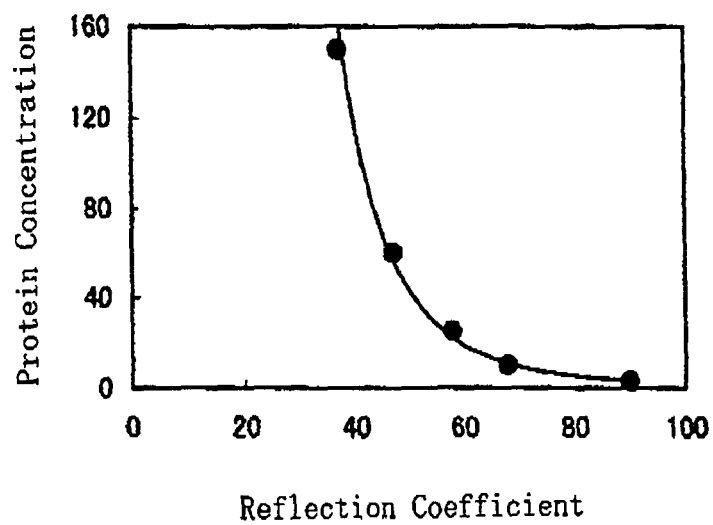
FIG. 1 is a graph showing a relationship between reflection coefficients measured by protein error method and protein concentrations measured by a pyrogallol red method.

The present invention relates to a technique for eliminating the influence of creatinine on a protein measurement which is based on coloring of a liquid sample coexisting with a protein measurement indicator. Specifically, according to the protein measuring method of the present invention, information reflecting creatinine concentration in the liquid sample is obtained, and then, based on this information, the influence of creatinine on the measurement of the protein concentration is eliminated. The present invention is applicable to liquid samples of urine, blood, and cerebrospinal fluid for example. The present invention is also applicable to any protein-containing liquid, such as a protein beverage and industrial wastewater. A typical example of protein as the target of measurement according to the present invention is albumin. Besides albumin, other proteins such as globulin and Bence-Jones protein can be measured by the present invention.

The method of measuring a protein according to the present invention includes: a first step of obtaining a first response value which reflects a protein concentration in a liquid sample, based e.g. on coloring given by a system in which the liquid sample and a protein measurement indicator coexist; a second step of obtaining a second response value which reflects a creatinine concentration in the liquid sample in a system containing the liquid sample but not any protein measurement indicator; and a third step of calculating the concentration of the protein in the liquid sample. This calculation is conducted in consideration of the second response value and based on the first response value.

In the first step, the first response value is obtained through a first protein measurement procedure (e.g. dye binding method or protein error method).

The dye binding method in the present invention refers to a method of measuring a protein which utilizes a phenomenon that protein bound with a dye (indicator) shifts the dye's maximum absorption wavelength. Examples of the dye include halogenated xanthene dyes and Coomassie Brilliant Blue. Among these indicators, it is preferable to use a halogenated xanthene dye. Usable halogenated xanthene dyes have the chemical structure expressed by Chemical Formula 1.

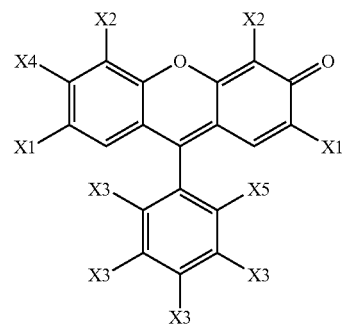

Chemical Formula 1

In Chemical Formula 1, X1 represents a halogen, a nitro group or a nitroso group, X2 represents a halogen, X3 represents a halogen or hydrogen, X4 represents a hydroxyl group or its salt, X5 represents a carboxyl group or its salt.

Preferred halogenated xanthene dyes according to the present invention are those expressed by Chemical Formula 1, with X1 provided by iodine, bromine, chlorine or a nitro group, X2 provided by iodine or bromine, X3 provided by chlorine, bromine or hydrogen. The most preferred are those with X1 and X2 provided by iodine or bromine, and X3 provided by chlorine. Examples of salt for X4 and X5 are sodium salts typically.

Preferred halogenated xanthene dyes according to the present invention are those expressed by Chemical Formulas 2 through 6. In particular, it is preferable to use protein measurement indicators expressed by Chemical Formulas 2 and 3.

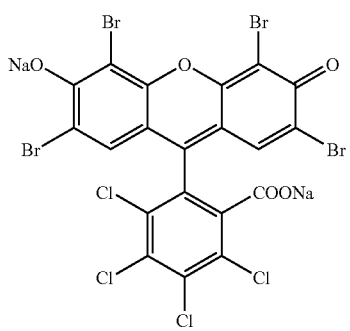

Chemical Formula 2

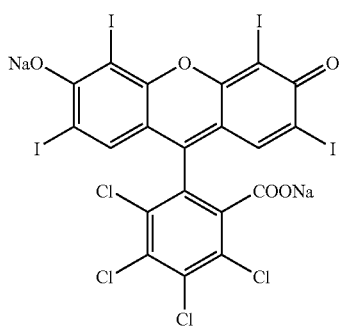

Chemical Formula 3

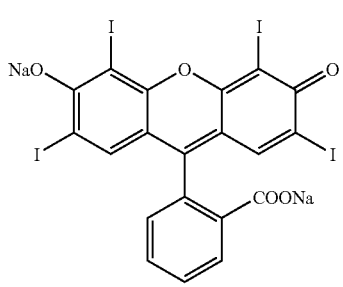

Chemical Formula 4

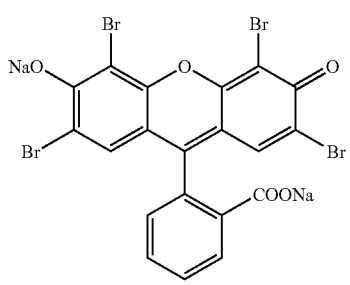

Chemical Formula 5

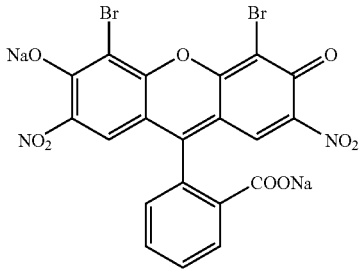

Chemical Formula 6

The halogenated xanthene dyes represented by Chemical Formulas 2 through 6 can be obtained easily from the manufacturers listed in Table 1.

TABLE 1

|  | Brand Name | Manufacturer |
| --- | --- | --- |
| Chemical Formula 2 | Phloxine B | Tokyo Chemical Industry Co., Ltd. (Japan) |
| Chemical Formula 3 | Rose Bengal | Tokyo Chemical Industry Co., Ltd. (Japan) |
| Chemical Formula 4 | Erythrosine B | Tokyo Chemical Industry Co., Ltd. (Japan) |
| Chemical Formula 5 | Eosin Y | Wako Pure Chemical Industries, Ltd. (Japan) |
| Chemical Formula 6 | Eosin B | Tokyo Chemical Industry Co., Ltd. (Japan) |

The protein error method in the present invention refers to a method of measuring a protein which utilizes a phenomenon that a protein error indicator, which is a type of pH indicator, gives a color at a higher pH than the true pH in proportion to the amount of protein contained in the sample. Examples of the protein error indicator are triphenylmethane dyes. Specific examples of the triphenylmethane dyes include Tetrabromophenol Blue (TBPB), Bromochlorophenol Blue (BCPB), and Bromophenol Blue (BPB), with Tetrabromophenol Blue (TBPB) being most typical.

In the second step of the present invention, the second response value is measured in accordance with e.g. enzyme method, Jaffe method, copper chelate oxidation method, palladium complex competition method, or Benedict method.

The enzyme method is a method of measuring creatinine from the amount of a product created by reaction between creatinine and an enzyme. Examples of the enzyme used in this method include creatinine deaminase and creatinine amidohydrolase (creatininase). When the former enzyme is used, ammonia is generated from creatinine by the activity of creatinine deaminase, and the amount of creatinine is measured from the amount of ammonia. On the other hand, when the latter enzyme is used, creatine is generated from creatinine by the activity of creatinine amidohydrolase (creatininase), and the amount of creatinine is measured from the amount of creatine. The amount of creatinine is measured by causing the creatine to act with creatine amidinohydrolase, sarcosine oxidase and peroxidase, thereby producing hydrogen peroxide, and then the hydrogen peroxide is led to a coloring system for measurement of the creatine.

Jaffe method is a method of measuring creatinine by measuring the brown coloration caused by a reaction between creatinine and picric acid under alkaline conditions.

The copper chelate oxidation method is a method of measuring creatinine by utilizing a reaction in which copper and creatinine form a complex under neutral conditions, showing peroxidase activity.

The palladium complex competition method is a method of measuring creatinine based on a change in a dye's maximum absorption wavelength when a complex between palladium and the dye is present with creatinine. The method is detailed in the JP-A 2004-138407 Gazette. An example of the dye which is to be used for this method is Chromazurol S (2,6-Dichloro-4'-hydroxy-3',3"-dimethylfuchsone-5',5"-dicarboxylic acid, disodium salt).

The Benedict method is a method of quantifying creatinine by utilizing a reaction (Benedict reaction) between Benedict's reagent and creatinine under alkaline conditions.

In the third step, the protein concentration is calculated based on a predetermined calibration curve. The calibration curve can be made by a method which includes: a step of obtaining a plurality of responses for each of a plurality of liquid samples, based on a first protein measurement procedure; a step of measuring a protein concentration in each of the liquid samples based on a second protein measurement procedure which is less susceptible to creatinine influence than the first protein measurement procedure; and a step of relating the responses to the protein concentrations measured by the second protein measurement procedure.

Examples of the second protein measurement procedure include immunoturbidimetric method, immunolatex agglutination method, and ternary complex method.

The immunoturbidimetric method is a method of measuring an antigen (protein) based on turbidity caused by a lattice crystal formed in a reaction between the antigen (protein) and its antibody. The antibody is selected in accordance with the kind of target protein for the measurement. For example, when measuring albumin, a monoclonal antibody or a polyclonal antibody is used.

The immunolatex agglutination method is a method of measuring a protein based on turbidity caused by flocculant production formed in a reaction between the protein and an immune reactant which is specially reactive thereto and is born by latex microparticles.

The ternary complex method is a method of measuring a protein based on the color of a dye-metal complex, in a reaction between the protein and the complex. Examples of the metal which forms a complex with dye include indium, molybdenum, cobalt, copper, and nickel.

Examples of the dye which forms a complex with indium include polyhydroxybenzene sulfonephthalein dyes and polyhydroxybenzene phthalein dyes. Typical examples are pyrocatechol violet, pyrogallol red, Bromopyrogallol red, xylenol orange, pyrogallol phthalein and o-hydroxyhydroquinone phthalein.

Examples of the dyes which form a complex with molybdenum complex includes: pyrogallol red, Bromopyrogallol red, o-hydroxyhydroquinone phthalein and gallein.

In the method of measuring a protein according to the present invention, the second step includes, for example, calculation based on the second response value, of the influence quantity of the amount of creatinine to the first response value whereas the third step includes calculation based on the first response value, of a preliminary value of the protein concentration, and calculation of a final protein concentration by subtracting the influence quantity of the amount of creatinine from the preliminary value.

In the second step, the creatinine influence quantity is calculated, based on a predetermined calibration curve. The calibration curve can be made by, for example, first measuring response values from a plurality of liquid samples having the same protein concentration but different creatinine concentration from each other, using the above-described first protein measurement procedure such as the dye binding method or the protein error method, and then relating these response values to the creatinine concentrations.

In the method of measuring a protein according to the present invention, the third step may include: obtainment of a corrected response value by correcting the first response value based on the first and the second response values; and calculation of the protein concentration in the liquid sample, based on the corrected response value.

The corrected response value is calculated by arithmetic expression derived, for example, from a plurality of sample groups: Each sample group consists of a plurality of liquid samples having the same protein concentration but different creatinine concentration from each other, and each sample group has a different protein concentration from each other. The arithmetic expression is derived from a method which includes for example: a step of measuring a response value for each of the liquid samples in each sample group; a step of obtaining a relationship between the response values from the liquid samples and the creatinine concentrations in each sample group, as a plurality of relational expressions for all of the sample groups in the form of linear expression; and a step of obtaining a relationship between a gradient in each of the relational expressions and the response value from the liquid sample having a specific creatinine concentration in each sample group, in the form of relational expression.

When practicing the present measurement method, the liquid sample is supplied to a liquid reagent containing the protein measurement indicator, or to a solid reagent containing the protein measurement indicator. Preferably, however, the method in which the liquid sample is supplied to a solid reagent is used since it will help establishing an easier measurement procedure. A typical example of the solid reagent is one carried by test paper.

The test paper can be made by impregnating an absorbing carrier with an impregnating solution containing the reagent, a buffer and so on, and then drying the impregnated carrier. The test paper piece may be used as is or otherwise; e.g. as attached to a non-absorbent carrier formed of a synthetic resin for example.

There is no specific limitation to the concentration of the indicator in the impregnating solution. The concentration may depend on the kind of indicator used. A typical concentration range is 0.1 through 10 mM, and more preferably 0.5 through 2 mM.

The impregnating solution has a pH value slightly lower than the pKa value of the indicator. For example, if the indicator is provided by a halogenated xanthene dye, the solution should be in the range of pH=1.5 through 4.5, and more preferably of pH=2.0 through 3.5.

The buffer may be anything as long as it has a good buffering ability under the impregnating solution pH (e.g. pH=1.5 through 4.5), and does not inhibit the reaction between the protein measuring reagent and the protein. Examples of the buffer include glycine buffer solution, citric acid buffer solution, succinic acid buffer solution, malic acid buffer solution and tartaric acid buffer solution. There is no specific limitation to the concentration of the buffer in the impregnating solution. A typical concentration range is 0.1 through 1.5 M, and more preferably 0.3 through 1 M.

The absorbent carrier can be provided by a porous material which does not contain protein. The porous material may be in the form of paper, foam (polyfoam), woven cloth, non-woven cloth or knitted work. Materials for forming the absorbent carrier include cotton, linen, cellulose, cellulose nitrate, acetylcellulose, rock wool, glass fiber, silica fiber, carbon fiber, boron fiber, polyamide, aramid, polyvinyl alcohol, polyvinyl acetate, rayon, polyester, nylon, polyacrylic acid, polyacrylic acid ester, and polyolefin for example.

Example 1

In the present example, liquid samples of different protein concentrations were dripped to test paper impregnated with a protein error indicator, to obtain reflection coefficients. Comparative study was made between the reflection coefficient and the protein concentration of each liquid sample measured by a pyrogallol red method, which is one of the ternary complex methods.

The test paper was made by impregnating a filter paper (3MMChr, manufactured by Whatman plc), with an impregnating solution prepared by mixing 0.5 mM tetrabromophenol blue (TBPB), 0.5 M malic acid buffer solution (pH=3.4) and 30 wt % ethanol, and then drying the paper. The reflection coefficients were measured by colorimeter, based on a reflected light when the test paper was irradiated with a light whose peak wavelength was 630 nm.

The liquid samples were made by adding an appropriate amount of human serum albumin to low-creatinine-concentration, healthy-human urine which had a creatinine concentration not higher than 20 mg/dL. The amount of the liquid sample dripped to the test paper was 7 μL.

Results of the measurements on the reflection coefficients and the protein concentrations are given in FIG. 1, where the reflection coefficient is represented by the horizontal axis and the protein concentration is represented by the vertical axis. As understood from FIG. 1, there is a correlation between the reflection coefficient measured by the protein error indicator and the protein concentration and therefore, it is possible to measure the protein concentration by measuring the reflection coefficient. The correlation between the reflection coefficient (x(%)) and the protein concentration (y(mg/dL)) can be expressed by the following Mathematical Formula 1 using the least-square method.
Mathematical Formula 1

$$y=2*10^9*x^{-4.4653}$$

Example 2

In the present example, a plurality of liquid samples each having a different creatinine concentration from others were used, to study how the amount of creatinine influences the actual measurement of protein concentration.

The test paper was made following the same procedure as in Example 1. The reflection coefficients were measured by colorimeter, based on a reflected light when the test paper was irradiated with a light whose peak wavelength was 630 nm.

The protein concentrations were calculated by assigning the measured reflection coefficients to Mathematical Formula 1. On the other hand, the amounts of creatinine were measured by an enzyme method. In the enzyme method, creatinine amidohydrolase was used as the enzyme to generate creatine. Thereafter, creatine amidinohydrolase, sarcosine oxidase and peroxidase were added to the creatine, then the amount of creatine was quantified conventionally, in accordance with the standard method, and creatinine concentration was determined from the amount of creatine.

The liquid samples used had the same protein concentration and different creatinine concentration from each other. Each liquid sample was made by adding an appropriate amount of creatinine to low-creatinine-concentration, healthy-human urine which had a protein concentration of 5.3 mg/dL approx., and a creatinine concentration not higher than 20 mg/dL. The amount of the liquid sample dripped to the test paper was 7 μL.

Figure 2:
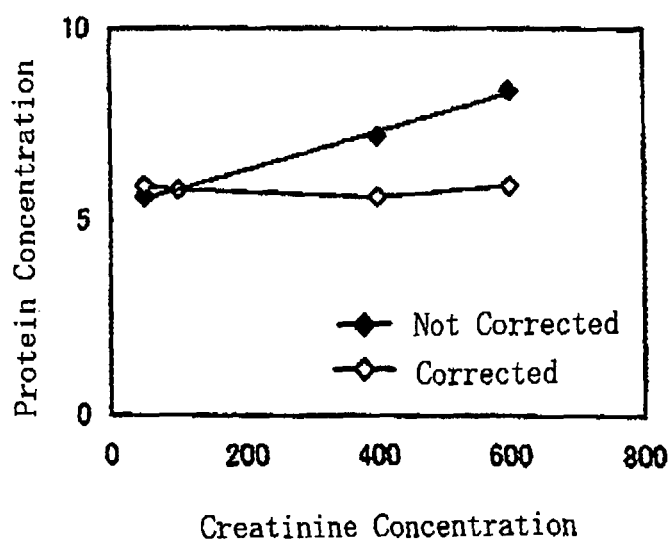
FIG. 2 is a graph showing calculated values of protein concentration before and after eliminating creatinine influences.

Results of the measurements on the creatinine concentrations and protein concentrations are given in FIG. 2, where the creatinine concentration is represented by the horizontal axis, and the protein concentration is represented by the vertical axis, using the symbol (♦). As understood from FIG. 2, with the actual protein concentration being consistent, a greater creatinine concentration will cause Mathematical Formula 1 to give a proportionally greater protein concentration. Specifically, it is observed that the reflection coefficient which is measured as a result of reaction between creatinine and the protein error indicator TBPB decreases whereas the calculated value is higher than the protein concentration. This means that once the creatinine concentration is found, it is possible to tell how much higher the calculated value is than the actual protein concentration, i.e. it is possible to tell the creatinine influence quantity.

Now, the relationship between the creatinine concentration (x (mg/dL)) in FIG. 2 and the calculated protein concentration (y (mg/dL)) based on Mathematical Formula 1 can be expressed by a proportional expression as the following Mathematical Formula 2, using the least-square method.
Mathematical Formula 2

$$y=0.0051i+5.3076$$

Further, the protein concentration (Y (mg/dL)) which is the value after eliminating the influence caused by the amount of creatinine can be given by the following Formula 3.
Mathematical Formula 3

$$Y=y-0.0051x$$

Now, healthy urine has an average creatinine concentration of 100 mg/dL. With this being a standard, the above Mathematical Formula 3 can be expressed as the following Mathematical Formula 4.
Mathematical Formula 4

$$Y=y-0.0051(x-100)$$

FIG. 2 also plots protein concentrations calculated by Mathematical Formula 4, using the symbol (◇). The protein concentrations calculated by Mathematical Formula 4 are substantially consistent regardless of the creatinine concentration, indicating that the influence from the amount of creatinine is eliminated.

Example 3

In the present example, a halogenated xanthene dye was carried in test paper. Liquid samples are dripped onto the test paper, and relationship between reflection coefficients and albumin concentrations measured by the immunoturbidimetric method was studied.

The test paper was made by the same way as in Example 1, differing only in that the protein measurement indicator was provided by a halogenated xanthene dye (Phloxine B, manufactured by Tokyo Chemical Industry Co., Ltd. (Japan)) represented by Chemical Formula 2. The reflection coefficients were measured by colorimeter, based on a reflected light when the test paper was irradiated with a light whose peak wavelength was 560 nm. The liquid samples were made in the same way as in Example 1.

The albumin concentration measurements using the immunoturbidimetric method were based quantification by means of optical absorbency observed when a light whose wavelength was 340 nm was applied to a reaction liquid resulted from the reaction between the antibody, which was provided by the monoclonal antibody, and albumin.

Figure 3:
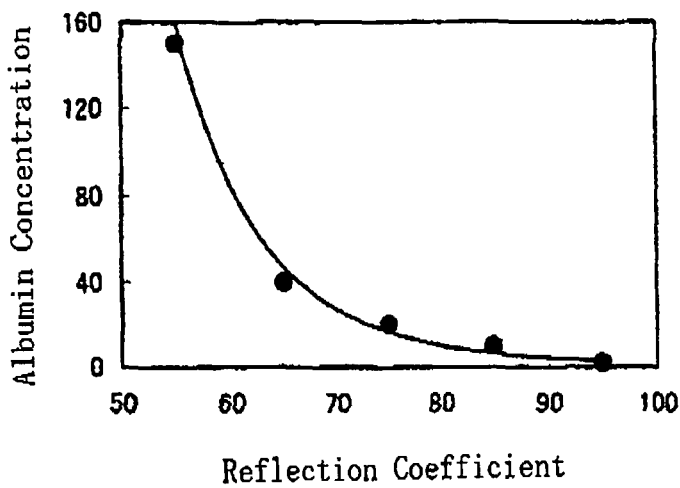
FIG. 3 is a graph showing a relationship between reflection coefficients measured by a dye binding method and albumin concentrations measured by an immunoturbidimetric method.

Results of the measurements on the reflection coefficients and the protein concentrations are given in FIG. 3, where the reflection coefficient is represented by the horizontal axis and the albumin concentration is represented by the vertical axis. As understood from FIG. 3, there is a correlation between the reflection coefficient measured by using the halogenated xanthene dye and the albumin concentration. Therefore, it is possible to obtain albumin concentration by measuring the reflection coefficient. The correlation between the reflection coefficient (x(%)) and the albumin concentration (y(mg/L)) can be expressed by the following Mathematical Formula 5, using the least-square method.

Mathematical Formula 5

$$Y=8*10^{14}*x^{-7.2932}$$

Example 4

In the present example, a plurality of liquid samples having different creatinine concentrations were used to study influences of the amount of creatinine on the reflection coefficients (the albumin concentrations which were actually measured).

The test paper was made by the same way as in Example 3. The reflection coefficients were measured by calorimeter, based on a reflected light when the test paper was irradiated with a light whose peak wavelength was 560 nm. The albumin concentrations were calculated by assigning the measured reflection coefficients to Mathematical Formula 5. The amounts of creatinine were measured by the enzyme method as in Example 2.

The liquid samples used had the same protein concentration and different creatinine concentration from each other. Two kinds of liquid samples were made: by adding an appropriate amount of creatinine to low-creatinine-concentration, healthy-human urine having a creatinine concentration not higher than 20 mg/dL (low-albumin samples); and by adding human serum albumin to the above-described healthy-human urine in addition to an appropriate amount of creatinine (high-albumin samples). The amount of the liquid sample dripped to the test paper was 7 µL.

Figure 4:
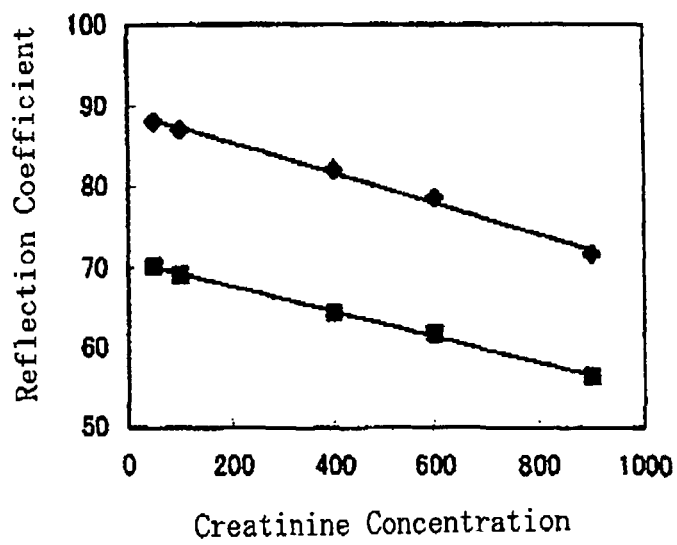
FIG. 4 is a graph showing how the amount of creatinine influences on reflection coefficient measurements, demonstrated by using a low-albumin sample and a high-albumin sample.

Results of the measurements on the creatinine concentrations and reflection coefficient are given in FIG. 4. In FIG. 4, the creatinine concentration is represented by the horizontal axis and the reflection coefficient is represented by the vertical axis. The measurements on the low-albumin samples are plotted with the symbol (♦) whereas those on the high-albumin samples are plotted with the symbol (■). As understood from FIG. 4, with the actual albumin concentration being consistent, a greater creatinine concentration will give a proportionally smaller reflection coefficient. The result means that creatinine reacts with the halogenated xanthene dye, decreasing the measured reflection coefficient while increasing the calculated value beyond the actual protein concentration. Simultaneously, this means that once the creatinine concentration is found, it is possible to tell how much higher the calculated value is than the actual protein concentration, i.e. it is possible to tell the creatinine influence quantity.

Now, the relationship between the creatinine concentration (x (mg/dL)) and the reflection coefficient (y (%)) can be expressed by Mathematical Formula 6(1) for the low-albumin samples and by Mathematical Formula 6(2) for the high-albumin samples, using the least-square method.

Mathematical Formulas 6

$$y=-0.0188x+89.135 \quad (1)$$

$$y=-0.0158x+70.837 \quad (2)$$

Figure 5:
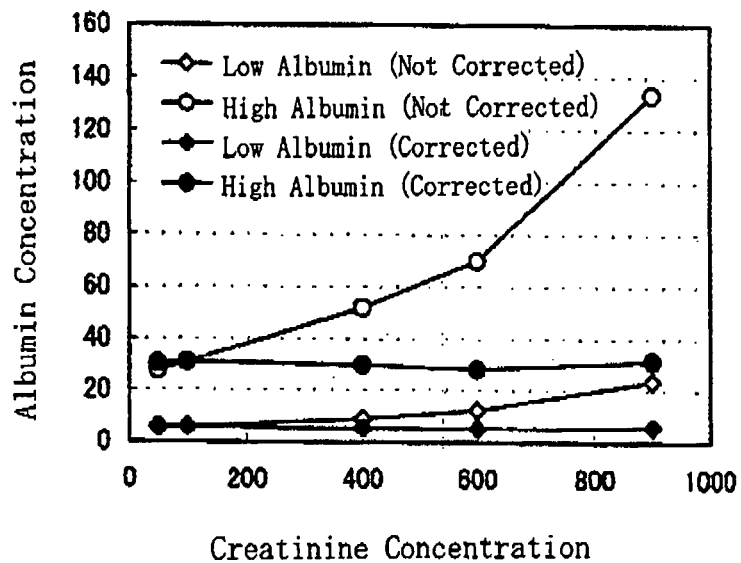
FIG. 5 is a graph showing calculated values of albumin concentration before and after eliminating creatinine influence, demonstrated by using a low-albumin sample and a high-albumin sample.

In Mathematical Formula 6-(1) and Mathematical Formula 6-(2), it should be noted that a different albumin concentration will give a different gradient. Specifically, in Mathematical Formula 6-(1) and Mathematical Formula 6-(2) the gradient is the index which shows the extent of influence caused by the amount of creatinine. The different gradients mean that a different albumin concentration will result in a different creatinine influence quantity. This point is also understood from the fact in FIG. 3 that the relationship between albumin concentration and reflection coefficient is not linear, and there is a lower limit in the value of reflection coefficient. FIG. 5 shows results of albumin concentration calculations by Mathematical Formula 5 from actually measured reflection coefficients from the low-albumin samples and the high-albumin samples. In FIG. 5, the results from the low-albumin samples are plotted with the symbol (◊) whereas those from the high-albumin samples are plotted with the symbol (○). As understood from FIG. 5, in both of the low-albumin samples and the high-albumin samples, a greater creatinine concentration will give a greater calculated albumin concentration. In addition, the high-albumin samples are under greater influence from creatinine than the low-albumin samples. In other words, the influence from the amount of creatinine can be eliminated by correcting the measured reflection coefficient in accordance with the albumin concentration thereby canceling the creatinine influence quantity, before calculating the albumin concentration based on Mathematical Formula 5.

Figure 6:
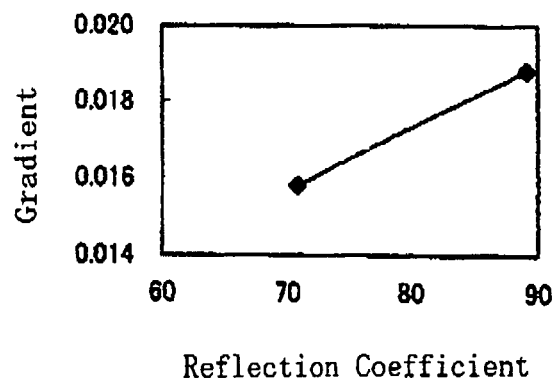
FIG. 6 is a graph showing a relationship between reflection coefficients when creatinine concentration is 100 mg/dL and absolute values of gradient in the graph in FIG. 4.

FIG. 6 shows a graph, where the horizontal axis represents the reflection coefficient (x(%)) when the creatinine concentration is 100 mg/dL, and the vertical axis represents the absolute value of the gradient (y(-)) in Mathematical Formula 6(1) and Mathematical Formula 6(2). The graph in FIG. 6 can be represented by the following Mathematical Formula 7.

Mathematical Formula 7

$$y=0.0002x+0.0042$$

Therefore, the correction formula for the reflection coefficient (R'(%)) which takes into account the influence from the amount of creatinine in accordance with albumin concentration can be expressed as the following Mathematical Formula 8. In Mathematical Formula 8, "R" represents the reflection coefficient (%) from actual measurements whereas "Cre" represents creatinine concentration (mg/dL).

Mathematical Formula 8

$$R'(\%)=R+(0.0002R+0.0042)\times Cre$$

With the above, and with an average creatinine concentration of 100 mg/dL in healthy urine being a standard, Mathematical Formula 8 can be expressed as the following Mathematical Formula 9.

Mathematical Formula 9

$$R'(\%)=R+(0.0002R+0.0042)\times(Cre-100)$$

FIG. 5 also shows calculation results of the albumin concentration in which the reflection coefficient was first corrected by using Mathematical Formula 9 and then the albumin concentration was calculated by using Mathematical Formula 5. In FIG. 5, the symbol (♦) represents calculation results for the low-albumin samples whereas the symbol (●) represents calculation results for the high-albumin samples. As understood from FIG. 5, the albumin concentrations calculated by Mathematical Formula 5 using the reflection coefficient R' corrected by Mathematical Formula 9 are substantially consistent regardless of the creatinine concentration in both of the low-albumin samples and the high-albumin samples, indicating that the influence from the amount of creatinine is eliminated.

It is contemplated that the advantages demonstrated in Examples 1 through 4 will also be seen as long as creatinine reacts with a protein measurement indicator, i.e. when Mathematical Formula 1 and Mathematical Formula 5 are established from other methods of protein measurement, and/or the creatinine measurement method is provided by e.g. Jaffe method, copper chelate oxidation method, palladium complex competition method, and Benedict method.

The invention claimed is:

1. A method of measuring a protein in a liquid sample that also contains creatinine, the method comprising:
    a step of mixing a quantity of the liquid sample with a protein measurement indicator to form a first liquid system in which the protein and the creatinine react with the protein measurement indicator, wherein the protein measurement indicator is a halogenated xanthene dye or a triphenylmethane dye;
    a step of obtaining a first response value that reflects a protein concentration in the liquid sample, based on coloring of the protein measurement indicator caused by a reaction between the protein and the protein measurement indicator under influence of a reaction between the creatinine and the protein measurement indicator;
    a step of preparing another quantity of the liquid sample that does not contain the protein measurement indicator;
    a step of obtaining a second response value that reflects a creatinine concentration in the another quantity of the liquid sample; and
    a step of calculating a protein concentration in the liquid sample, by using the first response value and the second response value, for eliminating a measurement error caused by the reaction between the creatinine and the protein measurement indicator in the first liquid system.

2. The method according to claim 1, wherein the step of obtaining the second response value includes calculation of an error level included in the first response value, which is caused by the reaction between the creatinine and the protein measurement indicator, by using the second response value;
    the step of calculating the protein concentration includes calculation of a non-corrected protein concentration as a preliminary value from the first response value, and calculation of a corrected final protein concentration by subtracting the error level from the preliminary value.

3. The method according to claim 2, wherein the error level in the step of obtaining the second response value is calculated by using a predetermined calibration curve;
    the calibration curve being prepared in advance by measuring, in accordance with a dye binding method or a protein error method, response values with a plurality of known liquid samples each including protein of an identical concentration and creatinine of a different concentration from that of all other known liquid samples, and then obtaining correlation between the response values and the creatinine concentrations.

4. The method according to claim 1, wherein in the step of calculating the protein concentration in the liquid sample, a corrected response value of the first response value is obtained by using the measured first response value and the second response value, and the protein concentration in the liquid sample is calculated by using the corrected response value,
    wherein the corrected response value is calculated by using an arithmetic expression derived from a plurality of sample groups;
        each sample group consisting of a plurality of known liquid samples including the protein of an identical concentration and the creatinine of a different concentration from that of all other known liquid samples in the sample group, and
        the sample group including protein of different concentrations from that of all known liquid samples in other sample groups, and
        the arithmetic expression being derived from a method comprising:
        a step of measuring a response value for each of the known liquid samples in each sample group;
        a step of obtaining a relationship between the response values obtained from the known liquid samples and the creatinine concentrations in each sample group as relational expression for all of the sample groups in a form of linear expression; and
        a step of obtaining a relationship between a gradient in each of the relational expressions and the response value from the known liquid sample having a specific creatinine concentration in each sample group, in the form of relational expression.

5. The method according to claim 1, wherein the first response value is obtained in accordance with a first protein measurement procedure provided by a dye binding method or a protein error method.

6. The method according to claim 1, wherein the second response value is obtained in accordance with an enzyme method, Jaffe method, a copper chelate oxidation method, a palladium complex competition method, or Benedict method.

7. The method according to claim 5, wherein in the step of calculating the protein concentration, the protein concentration is calculated by using a predetermined calibration curve;
    the calibration curve being made in advance by a method including:
    a step of obtaining a plurality of responses from a plurality of known liquid samples by the first protein measurement procedure; and
    a step of measuring a plurality of protein concentrations in the known liquid samples by a second protein measurement procedure, which is less susceptible to creatinine influence than the first protein measurement procedure;
    the calibration curve representing relation between the responses obtained by the first protein measurement procedure and the protein concentrations measured by the second protein measurement procedure.

8. The method according to claim 7, wherein the second protein measurement procedure comprises an immunoturbidimetric method, immunolatex agglutination method or ternary complex method.

9. The method according to claim 1, wherein the halogenated xanthene dye has a chemical structure expressed in following Chemical Formula 1;

Chemical Formula 1

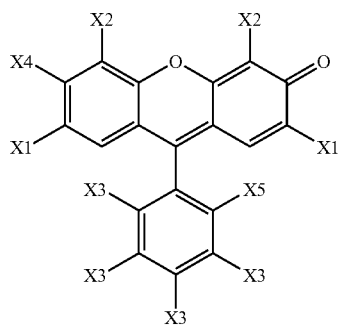

wherein in Chemical Formula 1, X1 represents a halogen, a nitro group or a nitroso group, X2 represents a halogen, X3 represents a halogen or hydrogen, X4 represents a hydroxyl group or its salt, and X5 represents a carboxyl group or its salt.

10. The method according to claim 9, wherein the halogenated xanthene dye has at least one chemical structure selected from the group consisting of the structures represented by following Chemical formulas 2 through 6:

Chemical Formula 2

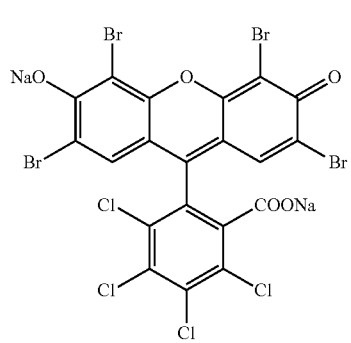

Chemical Formula 3

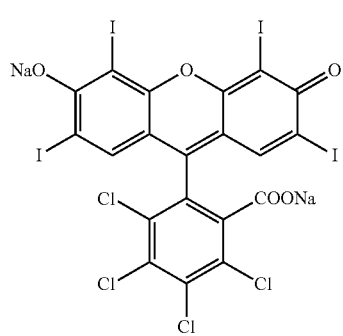

Chemical Formula 4

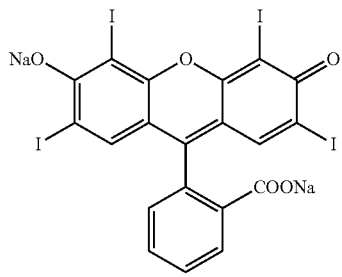

Chemical Formula 5

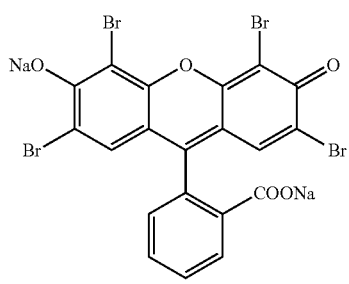

Chemical Formula 6

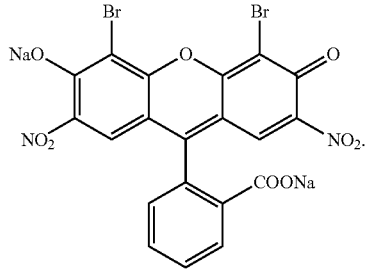

11. The method according to claim 1, wherein the triphenylmethane dye is Tetrabromophenol Blue (TBPB), Bromochlorophenol Blue (BCPB) or Bromophenol Blue (BPB).

12. The method according to claim 1, wherein the protein measurement indicator is held in a carrier in a dried form until being exposed to the liquid sample.

13. The method according to claim 1, wherein the protein is albumin.

14. The method according to claim 1, wherein the liquid sample is urine, blood, or cerebrospinal fluid.

* * * * *